US007671250B2

(12) United States Patent
Takahama

(10) Patent No.: US 7,671,250 B2
(45) Date of Patent: Mar. 2, 2010

(54) METHOD OF ACQUIRING IMMUNOLOGICAL TOLERANCE

(75) Inventor: Yousuke Takahama, Kokufucho (JP)

(73) Assignee: Japan Science and Technology Corporation, Kawaguchi-shi, Saitama (JP)

( * ) Notice: Subject to any disclaimer, the term of this patent is extended or adjusted under 35 U.S.C. 154(b) by 246 days.

(21) Appl. No.: 11/812,762

(22) Filed: Jun. 21, 2007

(65) Prior Publication Data

US 2008/0010694 A1    Jan. 10, 2008

Related U.S. Application Data

(62) Division of application No. 09/889,321, filed as application No. PCT/JP00/06379 on Sep. 19, 2000, now Pat. No. 7,276,234.

(30) Foreign Application Priority Data

Nov. 15, 1999  (JP)  ............................. H11-324771

(51) Int. Cl.
*A61K 48/00* (2006.01)
*A01K 67/027* (2006.01)
*C12N 5/10* (2006.01)
(52) U.S. Cl. .................. 800/8; 424/93.21; 435/325
(58) Field of Classification Search ............... 800/8; 424/93.21; 435/325
See application file for complete search history.

(56) References Cited

FOREIGN PATENT DOCUMENTS

| JP | 09-187470 | 7/1997 |
| JP | 09-194393 | 7/1997 |
| JP | 10-298101 | 11/1998 |

OTHER PUBLICATIONS

Oluwole et al. (1995) Cell. Immunol., vol. 162, 33-41.*
Ilan et al. (1996) J. Clin. Invest., vol. 98 (11), 2640-2647.*
DeMatteo et al. (1997) J. Virol., vol. 71 (7), 5330-5335.*
Yasufumi Kaneda et al., "Introduction and Expression of the Human Insulin Gene in Adult Rat Liver", *The Journal of Biological Chemistry*, Jul. 25, 1989, pp. 12126-12129, vol. 264, No. 21, The American Society for Biochemistry and Molecular Biology, Inc., U.S.A.
Keiko Kato et al., "Expression of Hepatitis B Virus Surface Antigen in Adult Rat Liver", *The Journal of Biological Chemistry*, Jul. 25, 1991, pp. 3361-3364, vol. 266, No. 6, The American Society for Biochemistry and Molecular Biology, Inc., U.S.A.
Naruya Tomita et al., "Direct In Vivo Gene Introduction into Rat Kidney", *Biochemical and Biophysical Research Communications*, Jul. 15, 1992, pp. 129-134, vol. 186, No. 1, Academic Press, Inc.
Naruya Tomita et al., "Hypertensive Rats Produced by In Vivo Introduction of the Human Renin Gene," Department of Geriatric Medicine, Osaka, Japan, *Circulation Research*, vol. 73, No. 5, Nov. 1993, pp. 898-905.

Yasufumi Kaneda et al., "Increased Expression of DNA Cointroduced with Nuclear Protein in Adult Rat Liver," *Science*, vol. 243, Jan. 20, 1989, pp. 375-378.
Ryuichi Morishita et al., "Evidence for Direct Local Effect of Angiotensin in Vascular Hypertrophy," *J. Clin. Invest.*, vol. 94, Sep. 1994, pp. 978-984.
Tessa Crompton et al., "The MAP Kinase Pathway Controls Differentiation from Double-Negative to Double-Positive Thymocyte", *Cell*, Jul. 26, 1996, pp. 243-251, vol. 86, Cell Press.
A.M.P. Behara et al., "Intrathymic Implants of Genetically Modified Fibroblasts," *The FASEB Journal*, vol. 6, Jul. 1992, pp. 2853-2858.
Ronald P. Dematteo et al., "Gene Transfer to the Thymus" *Annals of Surgery*, 1995, pp. 229-242, vol. 222, No. 3, Lippincott-Raven Publishers.
Yaron Ilan et al., "Induction of Central Tolerance by Intrathymic Inoculation of Adenoviral Antigens into the Host Thymus Permits Long-Term Gene Therapy in Gunn Rats," *J. Clin. Invest.*, vol. 98, No. 11, Dec. 1996, pp. 2640-2647.
Takehiko Sugawara et al. "An Improved Retroviral Gene Transfer Technique Demonstrates Inhibition of CD4-CD8-thymocyte Development by Kinase-Inactive ZAP-70", *The Journal of Immunologists*, 1998, pp. 2888-2894, vol. 161, The American Association of Immunologists.
Takehiko Sugwara et al., "Differential Roles of ERK and p38 MAP Kinase Pathways in Positive and Negative Selection of T Lymphocytes", *Immunity*, Oct. 1998, pp. 565-574, vol. 9, Cell Press.
Yutaka Hanazono et al., "In Vivo Marking of Rhesus Monkey Lymphocytes by Adeno- Associated Viral Vectors: Direct Comparison With Retro Viral Vectors", *Blood*, Oct. 1, 1999, pp. 2263-2270, vol. 94 No. 7.

(Continued)

*Primary Examiner*—Anne Marie S Wehbe
(74) *Attorney, Agent, or Firm*—Venable LLP; Ann S. Hobbs; Robert Kinberg

(57) ABSTRACT

The aim of the present invention is to provide a method of acquiring immunological tolerance to a foreign DNA or its expression product whereby the foreign DNA such as a vector carrying a foreign gene incorporated thereinto or its expression product can be recognized not as non-self but as self; a method of sustaining a gene therapeutic effect whereby a rejection to a foreign DNA such as a vector carrying a foreign gene incorporated thereinto or its expression product can be avoided; and a non-human animal which has acquired immunological tolerance to a foreign DNA such as a vector carrying a foreign gene incorporated thereinto or its expression product. Fetal immature T lymphocytes transferred with a foreign DNA, such as a foreign gene-incorporated viral vector, are introduced into thymus and said foreign DNA is expressed in the thymus organ. The methods of transferring said foreign DNA into a fetal immature T lymphocyte include, for example, co-cultivating the fetal immature T lymphocytes with viral vector-infected virus producer cells.

6 Claims, 3 Drawing Sheets

OTHER PUBLICATIONS

Jie Gu et al., "A Murine Model for Genetic Manipulation Of The T Cell Compartment", *Experimental Hematology*, 1996, pp. 1432-1440, vol. 24.

Sanjai Sharma et al., "Efficient Infection Of A Human T-Cell Line And Of Human Primary Peripheral Blood Leukocytes With A Pseudotyped Retrovirus Vector", Oct. 1996, pp. 11842-11847, vol. 93, Proc. Natl. Acad. Sci. USA.

Gregory L. Evans et al., "Genetic Induction Of Immune Tolerance To Human Clotting Factor VIII in a Mouse Model For Hemophilia A", May 1998, pp. 5734-5739, vol. 95, Proc. Natl. Acad. Sci. USA.

* cited by examiner

F I G. 2
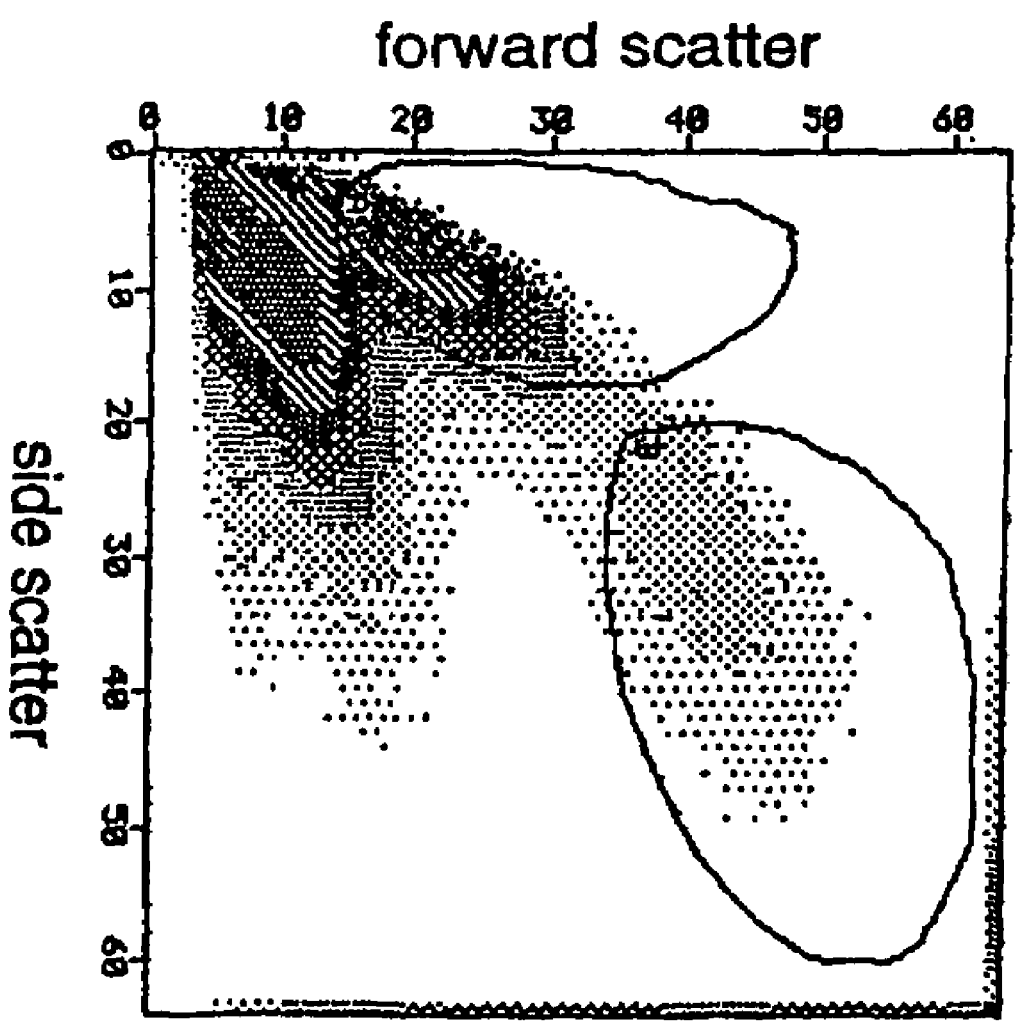

METHOD OF ACQUIRING IMMUNOLOGICAL TOLERANCE

This application is a divisional of U.S. application Ser. No. 09/889,321, filed Jul. 13, 2001, now U.S. Pat. No. 7,276,234 which is a 371 of PCT/JP00/06379, filed Sep. 19, 2000, and claims priority to Japanese application Japan 11-324771, filed Nov. 15, 1999, each of which is hereby incorporated by reference.

TECHNICAL FIELD

The present invention relates to a method of acquiring immunological tolerance, by fetal immature T lymphocyte-mediated DNA transfer into thymus, to a foreign DNA such as a viral vector-derived component and/or its expression product, a method of sustaining a gene therapeutic effect whereby a rejection raised in gene therapy to a foreign DNA and/or its expression product can be avoided, and a non-human animal such as a mouse or the like that has acquired immunological tolerance to a foreign DNA such as a viral vector-derived component and/or its expression product.

BACKGROUND OF THE INVENTION

A living organism generally does not display immune response to a self-composing antigen. This is called natural or innate immunological tolerance. On the other hand, even if an antigen is originally heterogeneous to a living organism, it may not react to the immune response which is displayed on dosing of the antigen, depending on when it is dosed (especially at viviparous period and neonatal period), how it is dosed (for example using immunosuppressant), and in what form it is dosed (e.g. a denatured substance is removed before dosing protein antigen). This is called acquired tolerance. Immune response is generally thought as celullar or humoral response to a non-self on having distinguished self from others (non-self). Self and non-self is distinguished by an antigen receptor located on the lymphocyte surface. When a substance is recognized as being non-self, lymphocytes proliferate to demonstrate cytotoxicity or produce antibody to the substance. However, at the primary recognition stage by lymphocytes, a step is necessary in which a foreign substance (non-self) is incorporated into dendritic cells or macrophages, and is then presented in a way as to be recognized by T lymphocytes. Thus the self/non-self recognition is thought to occur at the interaction level of dendritic cells or macrophages, and T lymphocytes.

Meanwhile, gene therapy, in which a foreign gene, obtained from such as recombinant DNA experiments is transferred into a patient's somatic cell in order to treat the patient's gene disease, through the gene function, has now been applied to various gene diseases such as cancer, immunodeficiency, cardiovascular diseases, or the like. But what prevents gene therapy most from being brought in practice is the immune responsiveness to a component of a vector (a vehicle for gene transfer) used for gene transfer, as mentioned above. In other words, the technique of gene transfer into cells has almost been completed, but the problem remains in that a vector should be used anyway for gene transfer. The known gene transfer methods using a vector involve viral vector methods using various kinds of virus systems such as retrovirus, adenovirus, lentivirus and the like; liposome methods in which a membrane encompassing DNA is fused with the cell; microinjection methods wherein a gene is transferred directly into the cell; and a method using Sendai virus (HVJ) which shows high affinity with the cell, wherein the size of inserting DNA will not be restricted (J. Biol. Chem. 264, 12126-12129, 1989, J. Biol. Chem. 266, 3361-3364, 1991, Bioche. Biophys. Res. Commun. 186, 129-134, 1992, Circ. Res. 73, 898-905, 1993, Science 243, 375-378, 1989, J. Clin. Invest 94, 978-984, 1994).

In any of the above mentioned gene transfer techniques, a transfer vector is foreign to human body, thus immune response is caused to the vector component resulting in the rejection of the vector by the living body sooner or later (generally within two weeks to a month). In case of viral vector, for example, a vector component is expressed as a protein in the infected cell, which protein subsequently is expressed as a peptide on the cell surface. The vector-derived peptide is then recognized by T lymphocytes that consequently kill the infected cell so that the vector (virus) is rejected. Thus the present gene therapy has succeeded in gene transfer itself, but a defect still remains that a long-sustaining effect has not successfully been attained.

Further, there are methods of acquiring immunological tolerance such as a method inducing immunological tolerance to mammal animals by not making them intake a fat-soluble component or a substance including fat-soluble component simultaneously with the antigen (Japanese Laid-Open Patent Application No. 9-194393). Also a method is known which uses a pharmaceutical preparation having a medicament as its effective component which has no substantial pharmacological effect when orally dosed, meanwhile showing the effect when injected, which effect, however, diminishes when injected repeatedly. Said pharmaceutical preparation is composed of a preparation for oral dose including the medicament with enough dose/unit to induce oral immunological tolerance and a preparation for injection including the medicament that is to be administrated after the oral immunological tolerance has been induced (Japanese Laid-Open Patent Application No. 10-298101). Furthermore there is a method which uses an artificial organ in order to establish immunological tolerance in the recipient. Said artificial organ is prepared by removing an organ from an animal showing specific immunological tolerance to the recipient. Thus peripheral immune mechanism composed of lymphocytes or the like of the transplanted organ will not attack human histocompatibility complex when transplanted to the recipient, which results in good survival of the transplanted organ (Japanese Laid-Open Patent Application No. 9-187470).

THE PROBLEM TO BE SOLVED BY THE INVENTION

The report (Cell 86, 243-251, 1996) describes a method of direct gene transfer mediated by retrovirus in FTOC (fetal thymus organ culture) and the role of MAP kinases in T lymphocyte development. Up to the present attempts have been made to transfer genes into thymus, which turned out to be so inefficient even when normal animals were used. These attempts displayed poor effect in suppressing a rejection caused by the existing T lymphocytes and it was not useful in practice (FASEB. J. 6, 2853-2858, 1992, Ann. Surg. 222, 229-242, 1995, J. Clin. Invest. 98, 2640-2647, 1996).

The present inventors performed transdermal or intraperitoneal injection to a mouse, an individual model animal which is to undergo gene therapy, with pGD-GFP, a combination of GFP (green fluorescent protein) gene and retroviral vector (pGD). They have found that the mouse displayed immune response to the vector component, which results in the diminishment of the viral vector carrying GFP gene within 2 weeks or a month. They have also found out that no immune response was observed when using immunodeficiency mouse deficient of T lymphocytes. This is because of T lymphocyte-mediated cellular immune response, that is T lymphocytes recognized a vector gene, which is useful for gene disease therapy, or its expression product as non-self and eliminated it.

The subject of the present invention involves providing: a method of acquiring immunological tolerance to a foreign DNA such as a vector carrying a foreign gene incorporated thereinto or its expression product, wherein a foreign DNA, such as a vector carrying a foreign gene useful for gene disease therapy, or its expression product is recognized as "self" and not as "non-self"; a method of sustaining a gene therapeutic effect whereby a rejection to a foreign DNA, such as a foreign gene-incorporated vector or its expression product can be avoided; and a non-human animal which has acquired immunological tolerance to a foreign DNA such as a foreign gene-incorporated vector or its expression product.

DISCLOSURE OF THE INVENTION

The present inventors have made a keen study on the method of avoiding immune response to a vector for gene transfer by re-educating the in vivo T lymphocyte system so as to in vivo T lymphocytes recognize the component of viral vector for gene transfer as "self", not as "non-self". They have found out the following through their study. With their gene transfer technique into fetal immature T lymphocyte in thymus (J. Immunol. 161, 2888-2894, 1998, Immunity 9, 565-574, 1998), a pGD-GFP gene was transferred into a mouse fetal immature T lymphocyte, which gene-transferred cell was purified through fluorescent staining using the GFP expression. Then a normal mouse was exposed to a low radiation to transiently suppress T lymphocytes of the mouse, subsequently the gene-transferred fetal immature T lymphocytes were introduced into its thymus. When the normal mouse had recovered from the radiation, it was transdermally or intraperitoneally injected with pGD-GFP retrovirus. As an effect of pre-treatment of fetal immature T lymphocytes, the expression of gene-transferred GFP in the mouse was sustained for a long period. This means anti-vector immune response was avoided and sustaining gene therapy could be conducted, and thus the present invention was completed.

Immune response to a foreign substance other than the vector component was kept normal in the above experiment. Therefore, it is made clear that the mouse immune system is not damaged as a whole, that the specific immunonogical tolerance to a vector for gene therapy is induced, and that a vector for gene transfer in other organs can be expressed without any problem right in fetal immature T lymphocytes. With this method, a gene can be transferred efficiently into thymus, a central organ for self/non-self recognition, by mediation of fetal immature T lymphocytes. This leads to an efficient expression of the vector component in thymus organ, wherefrom the efficient self-tolerance of T lymphocytes is established.

The present invention, therefore, relates to a method of acquiring immunological tolerance to a foreign DNA and/or its expression product characterized in that the foreign DNA is transferred into thymus mediated by fetal immature T lymphocytes; a method of acquiring immunological tolerance to a foreign DNA and/or its expression product, characterized in that a foreign-DNA-transferred fetal immature T lymphocyte is introduced into thymus organ and said foreign DNA is expressed in thymus organ; a method of acquiring immunological tolerance to a foreign DNA and/or its expression product, characterized in that the foreign DNA is DNA which at least comprises a gene coding for a substance causing allergic diseases or a substance causing auto-immune diseases; a method of acquiring immunological tolerance to a foreign DNA and/or its expression product, characterized in that the foreign DNA is DNA which at least comprises a gene coding for a peptide therapeutic medicament; a method of acquiring immunological tolerance to a foreign DNA and/or its expression product, characterized in that the foreign DNA is DNA which at least comprises a vector; a method of acquiring immunological tolerance to a foreign DNA and/or its expression product, characterized in that the vector is a viral vector for transferring a foreign gene; and a method of acquiring immunological tolerance to a foreign DNA and/or its expression product, characterized in that the viral vector is a vector derived from retrovirus, adenovirus, or lentivirus.

The present invention further relates to a method of sustaining a gene therapeutic effect characterized in that a foreign DNA in gene therapy is transferred into thymus mediated by fetal immature T lymphocytes; a method of sustaining a gene therapeutic effect, characterized in that immune response caused by a foreign DNA and/or its expression product is avoided by introducing a foreign-DNA-transferred fetal immature T lymphocyte in gene therapy into thymus, and by expressing a foreign DNA in thymus organ; a method of sustaining a gene therapeutic effect, characterized in that the foreign DNA is DNA which at least comprises a vector; a method of sustaining a gene therapeutic effect characterized in that the vector is a viral vector for transferring a foreign gene; and a method of sustaining a gene therapeutic effect characterized in that the viral vector is a vector derived from retrovirus, adenovirus, or lentivirus.

The present invention still further relates to a non-human animal that has acquired immunological tolerance to a foreign DNA and/or its expression product characterized in that the foreign DNA is transferred into thymus mediated by fetal immature T lymphocytes; a non-human animal that has acquired immunological tolerance to a foreign DNA and/or its expression product, characterized in that a foreign-DNA-transferred fetal immature T lymphocyte is introduced into thymus and said foreign DNA is expressed in thymus organ; a non-human animal that has acquired immunological tolerance to a foreign DNA and/or its expression product, characterized in that the foreign DNA is DNA which at least comprises a vector; a non-human animal that has acquired immunological tolerance to a foreign DNA and/or its expression product characterized in that the vector is a viral vector for transferring a foreign gene; a non-human animal that has acquired immunological tolerance to a foreign DNA and/or its expression product characterized in that the viral vector is a vector derived from retrovirus, adenovirus, or lentivirus; a non-human animal that has acquired immunological tolerance to a foreign DNA and/or its expression product, characterized in that the non-human animal belongs to rodents; and a non-human animal that has acquired immunological tolerance to a foreign DNA and/or its expression product characterized in that the non-human animal which belongs to rodents is a mouse.

BRIEF DESCRIPTION OF DRAWINGS

FIG. 2. A drawing showing the analytical result of gene-transferred fetal immature T lymphocytes and virus producer cells by forward and side scatter.

THE BEST MODE FOR CARRYING OUT THE INVENTION

Figure 1:
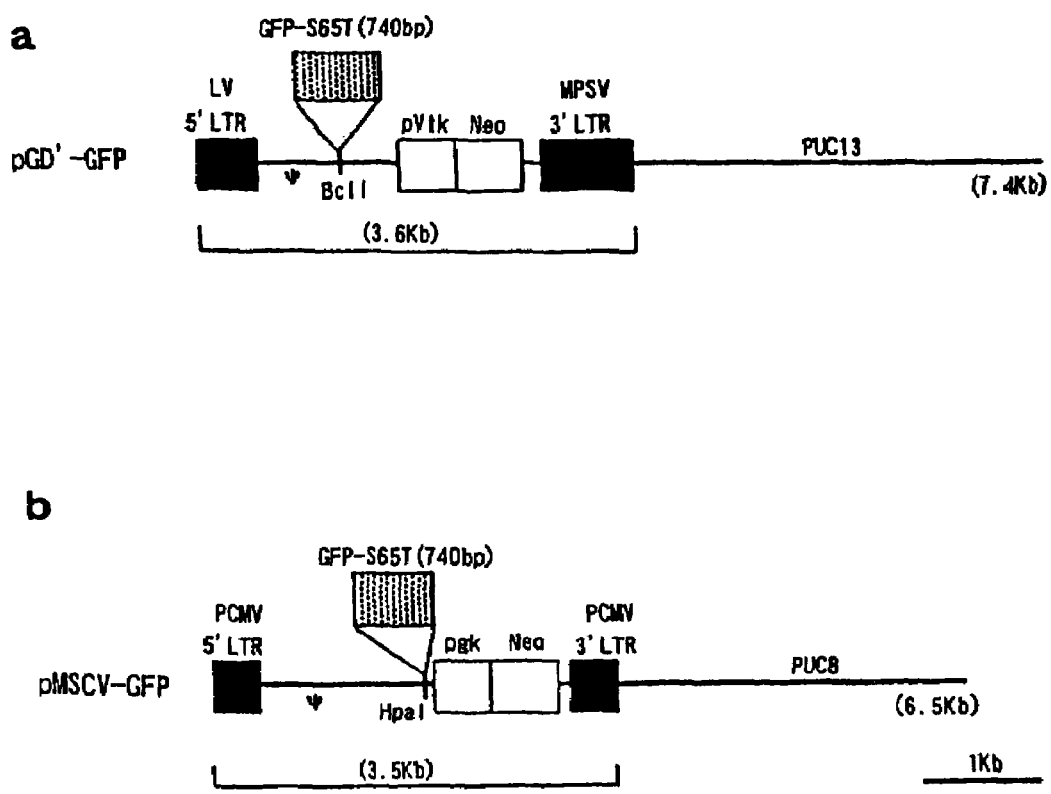
FIG. 1. A drawing showing the composition of the vector used for gene transfer of the present invention.

The method of the present invention for acquiring immunological tolerance to a foreign DNA and/or its expression product is characterized in that a foreign DNA is transferred into thymus mediated by fetal immature T lymphocytes. It is in particular characterized in that a fetal immature T lymphocyte, that has been transferred a foreign DNA, is introduced into thymus and said foreign DNA is expressed in thymus organ.

A foreign DNA of the present invention means DNA that does not originally exist in an animal which is to acquire immunological tolerance, wherein a translation product of the DNA is recognized as non-self to the animal. Also, a foreign gene of the present invention means a gene that does not originally exist in an animal which is to acquire immunological tolerance, wherein a translation product of the gene is recognized as non-self to the animal. As said foreign DNAs, such as a foreign gene, a vector, a vector incorporated with a gene of the interest, and the like are specifically exemplified. Also, the followings are enumerated as examples of foreign genes; such as genes coding for at least substances causing allergic or auto-immune diseases, especially genes coding for a substance causing serious allergic disease and a substance causing auto-immune diseases such as MBP (myelin basic protein) molecule that causes chronic rheumatoid arthritis (RA) or the like; and genes coding for at least a peptide anti-cancer agent, a peptide pharmaceutical medicament for diabetes, or the like. Further, a viral vector for such as transferring the above-mentioned foreign gene, a plasmid vector, a pharge vector, a yeast artificial chromosome (YAC) vector or the like are exemplified as vectors. Among these, viral vectors, especially viral vectors derived from such as retrovirus, adenovirus, or lentivirus are preferable in that they show considerably high transformation efficiency when infected as virus particle. When using one of these viral vectors, it is preferable to infect a host cell with the viral vector and to use it as a virus producer cell.

Fetal immature T lymphocytes of the present invention means T lymphocytes before they develop to mature T lymphocytes that express antigen receptors and functional co-receptors CD4/CD8, etc. It can be obtained, for instance, by fractioning/purifying from mature thymus lymphocytes, or from thymus lobes of embryonic day (ED) 14 to 18. Thymus lobes of embryonic day (ED) 14 to 15 exist at the upper heart such that left and right lobes exist individually. Thymus lobes at this stage is preferred to use in that they, being transparent spheres, are easy to be distinguished from peripheral organs and they do not allow mature T lymphocytes to immix.

As the methods of transferring a foreign DNA of the present invention into fetal immature T lymphocytes, the gene transfer technique (J. Immunol. 161, 2888-2894, 1998, Immunity 9, 565-574, 1998) developed by the present inventors is exemplified as a preferable one in that a foreign DNA-transferred cell can be differentiated/matured in thymus organ, an educational organ for T lymphocytes. Said technique involves a method wherein fetal immature T lymphocytes and virus producer cells are co-cultured; the gene-transferred fetal immature T lymphocytes are separated by forward and side scatter benefiting from their smaller size and lower density than those of virus producer cells; and fetal immature T lymphocytes having viability are separated/purified by fluorescence-activated cell sorter. The technique also involves a method that is carried out by separating/purifying the gene-transferred fetal immature T lymphocytes through distinguishing from fibroblast-derived virus producer cells by sorting GFP$^+$CD45$^+$ cells with flow cytometry cell sorter by using an antibody, which is stained, to hematopoietic cell marker CD45.

Immunological tolerance to an expression product of a foreign DNA of the present invention can be acquired, for instance, by the following procedures. A vector is transferred into a fetal immature T lymphocyte obtained by the methods described above, wherein the vector is incorporated with a gene of interest such as said foreign gene etc. The vector-transferred fetal immature T lymphocyte is then introduced into thymus by direct or intravenous injection into thymus followed by the expression of the foreign DNA in thymus organ, where, at the same time, immune response that was developed by the foreign DNA can be avoided The method of sustaining gene therapy effect is characterized in transfer of a foreign DNA of gene therapy into thymus by mediation of fetal immature T lymphocytes. Especially it is characterized in that immune response caused by a foreign DNA and/or its expression product can be avoided for a long time, i.e. more than a month, through introducing fetal immature T lymphocytes transferred with foreign DNA of gene therapy into thymus, thereby said foreign DNA is expressed in thymus organ. The sustenance of gene therapy effect will be attained when a foreign DNA useful for gene therapy is used as a foreign DNA in a method of acquiring immunological tolerance to the above-mentioned foreign DNA and/or its expression product.

A non-human animal of the present invention that have acquired immunological tolerance to a foreign DNA and/or its expression product is characterized in that the foreign DNA is transferred into thymus mediated by fetal immature T lymphocytes. Especially it is characterized in that an fetal immature T lymphocyte transferred with a foreign DNA is introduced into thymus, thereby said foreign DNA is expressed in thymus organ. As these non-human animals, non-human mammals such as mice, rats, rabbits or the like can be exemplified, among them, mice are most preferable because of the easiness in breeding or using them, and so on. The present invention is now demonstrated in more detail with the embodiments where a non-human animal is a mouse, but the technical scope of the invention is not limited to these embodiments.

Embodiment 1

Preparation of Culture Solution

Culture solution (10% FCS-RPMI1640) was prepared by adding 10% fetal calf serum (FCS), which was pre-treated for 30 min at 56° C., to RPMI1640 [a medium including at the final concentration, 50 μM 2-mercaptoethanol (Sigma Chemicals), 10 mM HEPES (Gibco BRL), 2 mM L-glutamine (Gibco BRL), 1× non-essential amino acids (Gibco BRL), 1 mM sodium pyruvate (Gibco BRL), 100 U/ml penicillin (Gibco BRL), and 100 μg/ml streptomycin (Gibco BRL)]. All of the procedures were performed under aseptic conditions in a clean hood.

Embodiment 2

Harvest of Mouse Fetal Thymus Lobes

Mice of pregnant day 15 or 16 were killed by cervical dislocation. Abdomens of mice were wiped with 70% ethanol, then fetus-filled uteri were taken out and placed on 100-mm sterilized dish. The fetuses were taken out from uteri and transferred to a 100-mm sterilized dish containing 20-30 ml medium of Embodiment 1. The blood and remaining debris were removed by swirling the dish gently for 2 or 3 times. The mice fetus was placed under a microscope. The chest of the fetus was gently opened and two thymus lobes were taken out, and they were placed on a gauze to remove the blood. Finally the mouse fetal thymus lobes were obtained.

Embodiment 3

Preparation of Culture Wells

A piece of sterilized Helistat sponge (Colla-Tec, Inc., Plainsboro, N.J. 08536) was placed in a culture well of a 24-well plate (16 mm diameter, sterilized). The culture well was added 1 ml medium of Embodiment 1. The smooth side of the sponge piece was faced up and a sterile PC (policarbonate) filter membrane (Costar, Nucleopore Corp. PC membrane, #110409, 113 mm diameter) was placed on the sponge. The filter membrane was flipped with forceps so that the both sides of the filter membrane were completely wet with the medium, subsequently 0.5 ml of the medium was gently removed from the well. The final medium was prepared to be 0.5 ml per well.

Embodiment 4

Organ Culture of Fetal Thymus Lobes 4 to 6 thymus lobes obtained from Embodiment 2 were placed on the filter membrane on the sponge in the culture well prepared in Embodiment 3, and then cultured in $CO_2$ incubator under the condition where the thymus lobes did not sink in the culture medium solution.

Embodiment 5

Preparation of Single-Cell Suspension after Organ Culture of Fetal Thymus

100 µl of the Staining buffer [phosphate buffer saline (PBS) including 0.2% bovine serum albumin (BSA) and 0.1% $NaN_3$, pH7.2] was dropped to the center of the reverse side of the lid of a 30-mm dish. The thymus lobes cultured in Embodiment 4 were transferred into the drop, and the number of lobes were counted using #7 forceps. Next, a small piece of nylon mesh (about 5 $mm^2$) was placed on the buffer into which the thymus lobes were transferred. Using 26-gauge needles with bent tips (top 5 mm, 90° angle) and 1-ml syringes, thymus lobes were gently teased while pushing the needles and syringes to the nylon mesh. The obtained single-cell suspension was transferred to a plastic tube in the syringes, then the number of the cells were counted to prepare a cell suspension of a given concentration.

Embodiment 6

Production of Virus Producer Cells

DNA of 740 bp encoding S65T mutant prepared from GFP gene (Clonetech) was cloned into BclI site of pGD' (FIG. 1a) or into HpaI site of pMSCV (FIG. 1b). The recombinant vector obtained by the cloning was transfected to GP+E–86 cells. $GFP^{high}$ clones were separated from G418 resistant cells using FACS Vantage cell sorter (Becton Dickinson). The diluent of filter supernatant obtained from separated clones were cultured for a day with G418 resistant cells of NIH-3T3 (ATCC CRL-1658), then the viral titer was measured. Virus producer cells (GP+E–86 cells infected with recombinant vector) with viral titer of more than $10^6$ CFU/ml were used in the embodiments below.

Embodiment 7

Production of Virus-Infected Fetal Immature T Lymphocytes

Suspension of single-cell fetal immature T lymphocytes, obtained in the above Embodiment 5, was pipette-transferred to a 96-flat well to finally make $0.5-2\times10^4$ fetal immature T lymphocytes per well. Subsequently the above-mentioned virus producer cells, pre-treated with trypsin and cultured for a day, were added $2-5\times10^3$ cells/well, and they were mixed in the well. The mixture was then cultured for 1-2 days in the presence of mouse recombinant IL-7 (interleukin 7; Genzyme) of final concentration 1-5 ng/ml, or in the additional presence of stem cell factor (SCF) of final concentration 1-5 ng/ml. The co-cultured fetal immature T lymphocytes were then gently pipette-recovered. The gene-transferred fetal immature T lymphocytes (area shown as FIG. 2a) were separated by forward and side scatter (FIG. 2) benefiting from smaller size and lower density of fetal immature T lymphocytes than those of producer cells, followed by separation/purification of viable fetal immature T lymphocytes by fluorescence-activated cell sorter (FACS).

Further, by sorting $GFP^+CD45^+$ cells by flow cytometry cell sorter using stained antibody to hematopoietic cell marker CD45, the gene-transferred fetal immature T lymphocytes were distinguished and separated/purified from fibroblast-derived virus producer cells.

Embodiment 8

Transferred-Gene Expression by Gene-Transferred Fetal Immature T Lymphocytes

Figure 3:
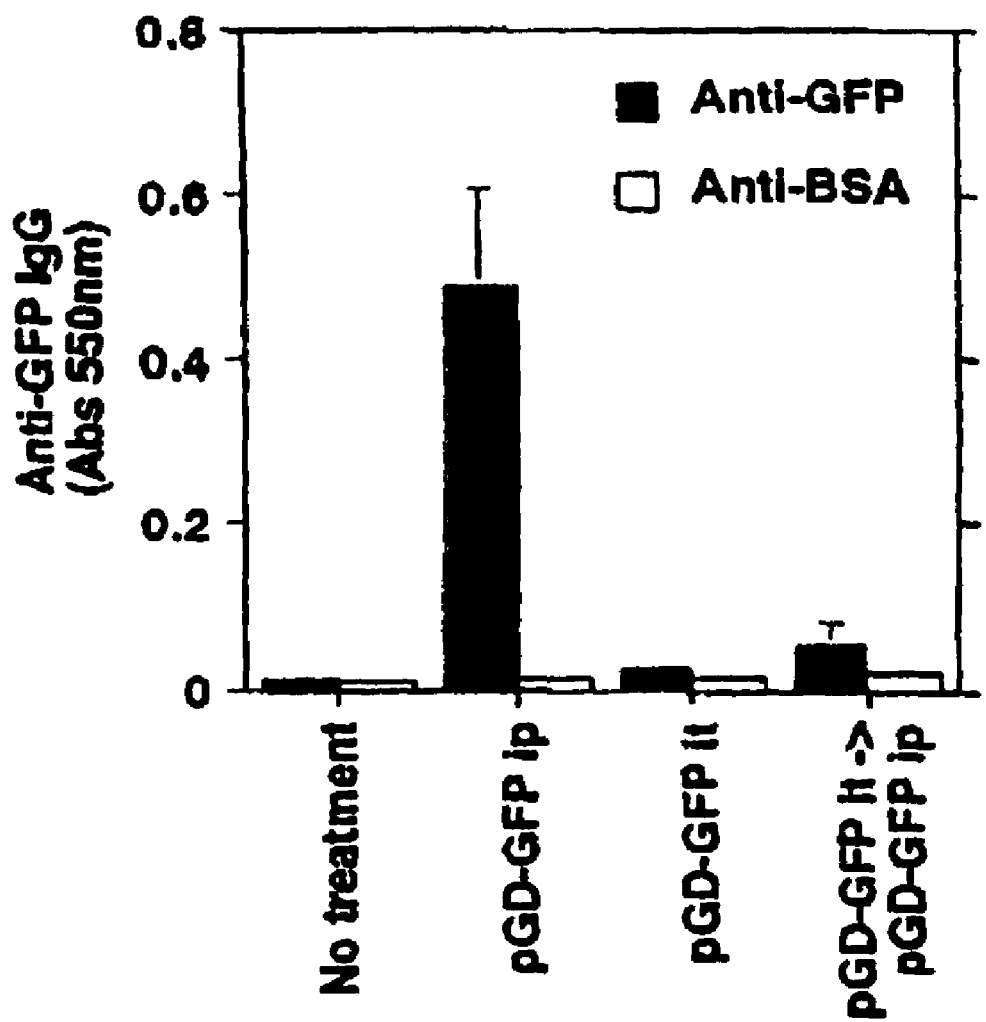
FIG. 3. A drawing showing the result of immune response of a mouse that is introduced with gene-transferred fetal immature T lymphocytes into its thymus.

Low level radiation was irradiated in order to transiently suppress T lymphocytes of a normal mouse (B6). Then the gene-transferred fetal immature T lymphocytes obtained in Embodiment 7 were introduced into thymus by direct injection thereinto. After the mouse was recovered from the radiation, splenocytes transferred with pGD-GFP retrovirus were intraperitoneally injected to the mouse, and anti-GFP antibody was analyzed 2 weeks later as antibody titer in blood using enzyme-antibody method. Anti-BSA (bovine serum albumin) antibody was also analyzed as control. The results are shown in FIG. 3. "No treatment" in FIG. 3 means antibody titer in blood of an innate normal mouse (B6), and it goes without saying that the antibody did not develop therein. "pGD-GFP ip" means antibody titer in blood when a normal mouse (B6) was intraperitoneally injected with pGD-GFP retrovirus-transferred splenocytes, wherein anti-GFP antibody development by GFP expression was observed. "pGD-GFP it" means antibody titer in blood of a mouse that was introduced gene-transferred fetal immature T lymphocytes into thymus (B6), obtained in Embodiment 7, when the mouse was intraperitoneally injected with pGD-GFP retrovirus-transferred splenocytes, and it can be observed that anti-GFP antibody scarcely developed in this mouse. "pGD-GFP it→pGD-GFP ip" means antibody titer in blood of a mouse that was introduced gene-transferred fetal immature T lymphocytes into thymus (B6), obtained in Embodiment 7, when the mouse was intraperitoneally injected with pGD-GFP retrovirus-transferred splenocytes, and it can be seen that anti-GFP antibody scarcely developed in this mouse. From the above results, the present inventors have confirmed the establishment of immunological tolerance to the component of viral vector-derived GFP in the mouse that was introduced with gene-transferred fetal immature T lymphocytes into thymus (B6), obtained in Embodiment 7. This means that anti-vector immune response can be avoided and enables long lasting gene therapy. It has also been confirmed that immune response to a foreign substance other than the vector component still remains normal so that the mouse immune system was not damaged as a whole, and that immunological tolerance specific to a vector for gene therapy was elicited.

INDUSTRIAL APPLICABILITY

The present invention enables to acquire immunological tolerance to a foreign DNA or its expression product by introducing fetal immature T lymphocytes transferred with a foreign DNA such as a foreign DNA-incorporated vector or the like into thymus, and by expressing said foreign DNA in thymus organ. Also, by the present invention, a rejecting response to the foreign DNA or its expression product can be avoided and gene therapeutic effect can be sustained for a long time in a stabilized condition. Further, a non-human animal that have acquired immunological tolerance to a foreign DNA such as a foreign DNA-incorporated vector of the present invention etc. or its expression product, are considerably useful for studying and developing gene therapy or the like.

What is claimed:

1. A non-human animal that has acquired immunological tolerance to a foreign DNA and/or its expression product produced by a method comprising: providing a fetal immature T lymphocyte transfected with the foreign DNA, irradiating a host mammal in order to transiently suppress T lymphocytes, and introducing the transfected fetal immature T lymphocyte into thymus of the host mammal, and subsequently expressing said foreign DNA in thymus organ during differentiation and maturation of the immature T lymphocyte in the thymus organ to reconstitute the immune system.

2. The non-human animal that has acquired immunological tolerance to a foreign DNA and/or its expression product according to claim 1, wherein the foreign DNA used for providing a fetal immature T lymphocyte transfected with foreign DNA at least comprises a vector.

3. The non-human animal that has acquired immunological tolerance to a foreign DNA and/or its expression product according to claim 2 wherein the vector comprising the foreign DNA used for providing a fetal immature T lymphocyte transfected with the foreign DNA is a viral vector for transferring a foreign gene.

4. The non-human animal that has acquired immunological tolerance to a foreign DNA and/or its expression product according to claim 3 wherein the viral vector is a vector derived from retrovirus, adenovirus, or lentivirus.

5. The non-human animal according to claim 1 that is a rodent.

6. The non-human animal according to claim 5 that is a mouse.

* * * * *

UNITED STATES PATENT AND TRADEMARK OFFICE
CERTIFICATE OF CORRECTION

| | |
|---|---|
| PATENT NO. | : 7,671,250 B2 |
| APPLICATION NO. | : 11/812762 |
| DATED | : March 2, 2010 |
| INVENTOR(S) | : Yousuke Takahama |

It is certified that error appears in the above-identified patent and that said Letters Patent is hereby corrected as shown below:

Title Page, Item (73) Assignee: should read as follows:

--(73) Assignee: Japan Science and Technology Agency, Kawaguchi-shi, Saitama (JP)--.

Signed and Sealed this

Twenty-fifth Day of May, 2010

David J. Kappos
*Director of the United States Patent and Trademark Office*